US010080751B2

(12) United States Patent
Huang

(10) Patent No.: US 10,080,751 B2
(45) Date of Patent: Sep. 25, 2018

(54) SYSTEMS AND METHODS FOR TREATING BACTERIAL INFECTION

(71) Applicant: Motif BioSciences Inc., New York, NY (US)

(72) Inventor: David Huang, Houston, TX (US)

(73) Assignee: Motif Biosciences Inc., New York, NY (US)

( * ) Notice: Subject to any disclaimer, the term of this patent is extended or adjusted under 35 U.S.C. 154(b) by 0 days.

(21) Appl. No.: 15/586,815

(22) Filed: May 4, 2017

(65) Prior Publication Data

US 2017/0319583 A1 Nov. 9, 2017

Related U.S. Application Data

(60) Provisional application No. 62/331,623, filed on May 4, 2016, provisional application No. 62/469,781, filed on Mar. 10, 2017.

(51) Int. Cl.
*A61K 31/506* (2006.01)
*A61K 9/00* (2006.01)
*A61K 9/08* (2006.01)
*A61K 31/501* (2006.01)

(52) U.S. Cl.
CPC .......... *A61K 31/506* (2013.01); *A61K 9/0019* (2013.01); *A61K 9/08* (2013.01); *A61K 31/501* (2013.01)

(58) Field of Classification Search
CPC .................................................... A61K 31/506
See application file for complete search history.

(56) References Cited

U.S. PATENT DOCUMENTS

| 5,773,446 A | 6/1998 | Masciadri | |
|---|---|---|---|
| 2009/0253722 A1* | 10/2009 | Gillessen | A61K 31/505 514/275 |

OTHER PUBLICATIONS

Morgan et al., Iclaprim: a novel dihydrofolate reductase inhibitor for skin and soft tissue infections, Future Microbiology, vol. 4, No. 2, 131-143, 2009.*
Andrews et al., Concentrations in plasma, epithelial lining fluid, alveolar macrophages and bronchial mucosa after a single intravenous dose of 1.6 mg/kg of iclaprim (AR-100) in healthy men, Journal of Antimicrobial Chemotherapy (2007) 60, 677-680.*
Barton et al., Future treatment options for Gram-positive infections-looking ahead, Clinical Microbiology and Infection, vol. 15, Supplement 6, Dec. 2009, pp. 17-25.*
Westreenen, New Antimicrobial Strategies in Cystic Fibrosis, Dec. 2010, vol. 12, Issue 6, pp. 343-352.*
NCT02600611, Nov. 6, 2015, available at https://clinicaltrials.gov/archive/NCT02600611/2015_11_06.*

Non-Final Office Action from corresponding U.S. Appl. No. 15/586,021 dated Jul. 19, 2017.
International Search Report and Written Opinion from Corresponding International Application No. PCT/US2017/031049 dated Jun. 22, 2017.
Hall 2$^{nd}$, RG, et al.,"Fractal Geometry-Based Decrease in Trimethoprim-Sulfamethoxazole Concentrations in Overweight and Obese People", *CPT Pharmacometrics Syst. Pharmacol.*, Nov. 21, 2016, pp. 674-681.
Anonymous, "NCT02607618 on Mar. 21, 2016: ClinicalTrials.gov Archive", Mar. 21, 2016, https://clinicaltrials.gov/archive/NCT02607618/2016_03_21, retrieved on Jun. 8, 2017, 3 pages.
McClain, Sarah L. et al., "Advances in the Medical Management of Skin and Soft Tissue Infections", *BMJ* (Clinical Research Edition), Dec. 14, 2016, vol. 355, p. i6004, 14 pages.
Krievins, D. et al., "Multicenter, Randomized Study of the Efficacy and Safety of Intravenous Iclaprim in Complicated Skin and Skin Structure Infections", *Antimicrobial Agents and Chemotherapy*, vol. 53, No. 7, May 4, 2009, pp. 2834-2840.
Arpida AG, "Arpida AG Iclaprim Concentrate for Solution for Infusion Advisory Committee Briefing Book", Anti-Infective Drugs Advisory Committee Meeting Tentatively Scheduled for Nov. 20, 2008, Nov. 20, 2008, https://www.fda.gov/ohrms/dockets/ac/08/briefing/2008-4394b3-03-ARPIDA.pdf, retrieved on Jun. 6, 2017, pp. 1-116.
Bach, Tiffany H. et al., "Present and Emerging Therapies for Methicillin-Resistant *Staphylococcus aureus* Skin and Soft Tissue Infections: Focus on Iclaprim", *Clinical Medicine Reviews in Therapeutics*, Jun. 1, 2011, pp. 191-201.
Food and Drug Administration, "Iclaprim for the Treatment of Complicated Skin and Skin Structure Infections", FDA Briefing Document for Anti-Infective Drugs Advisory Committee Meeting, Nov. 20, 2008, https://www.fda.gov/ohrms/dockets/ac/08/briefing/2008-4394b3-01-FDA.pdf, retrieved on Jun. 6, 2017, pp. 1-31.
Kohlhoff, Stephan A. et al., "Iclaprim", *Expert Opinion on Investigational Drugs*, vol. 16, No. 9, Sep. 22, 2007, pp. 1441-1448.
International Search Report and Written Opinion from Corresponding International Application No. PCT/US2017/030875, dated Jul. 11, 2017.
International Search Report and Written Opinion from Corresponding International Application No. PCT/US2017/031049, dated Jun. 22, 2017.
Anonymous, "NCT02600611 on Nov. 6, 2015: ClinicalTrials.gov Archive", Jun. 6, 2015, https://clinicaltrials.gov/archive/NCT02600611/2015_11_06, retrieved on Sep. 20, 2017, 3 pages.
Final Office Action from corresponding U.S. Appl. No. 15/586,021; dated Oct. 2, 2017.

(Continued)

*Primary Examiner* — Svetlana M Ivanova
(74) *Attorney, Agent, or Firm* — DLA Piper LLP (US)

(57) ABSTRACT

Therapeutic methods, kits, dosing regimens and uses of a medicament comprising iclaprim are provided, for example, for the treatment of bacterial infection. The administration of iclaprim in a fixed amount can achieve a Cmax(ss) below about 800 ng/mL, a T>MIC of between about 30% to about 95% and a ratio of AUC/MIC of about 20 to about 85, and the bacterial infection can be treated. The fixed amount can be about 70 mg to about 100 mg. The bacterial infection treated may be caused, or related to, drug-resistant bacteria including *S. pneumoniae, H. influenzae, S. aureus, K. pneumoniae* and *M. catarrhalis*. The bacterial infection may manifest as a skin and skin structure infection, pneumonia, asthma, emphysema and/or other adverse pulmonary conditions.

26 Claims, 1 Drawing Sheet

(56) References Cited

OTHER PUBLICATIONS

Advisory Action Before the Filing of an Appeal Brief from corresponding U.S. Appl. No. 15/586,021; dated Dec. 12, 2017.

* cited by examiner

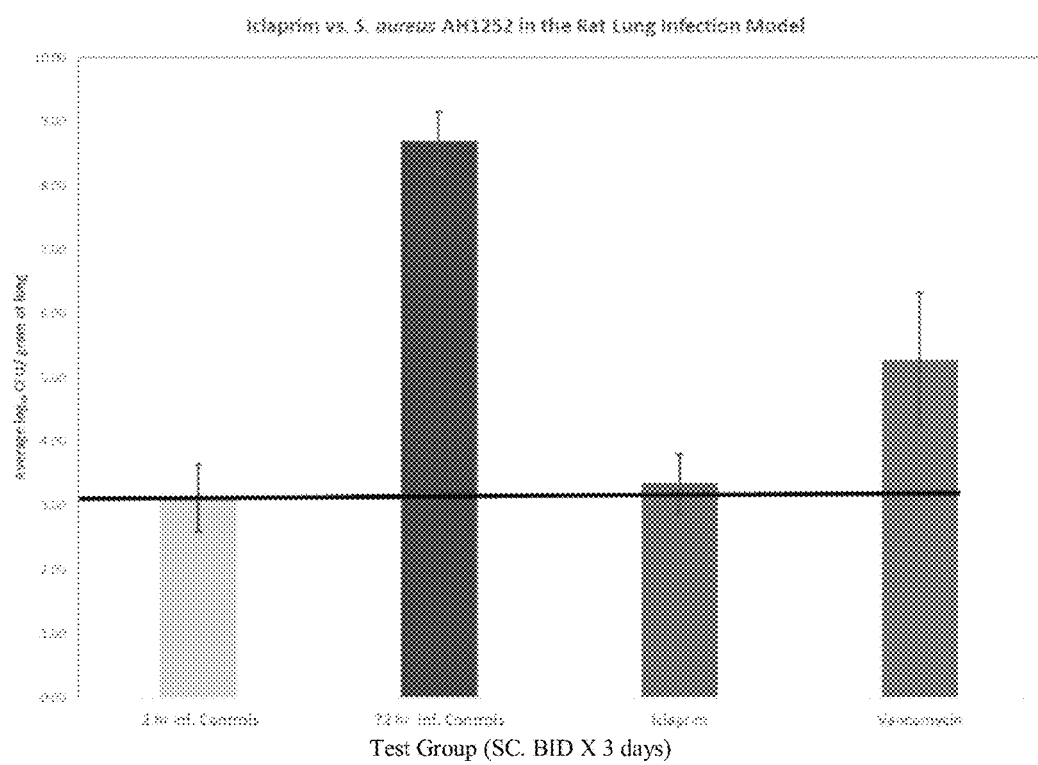

SYSTEMS AND METHODS FOR TREATING BACTERIAL INFECTION

TECHNICAL FIELD

Embodiments of the present disclosure relate generally to systems and methods for treating bacterial infection and, in particular, systems and methods comprising administration of iclaprim.

BACKGROUND

Iclaprim (MTF-100, which is also known as AR-100) is a potent inhibitor of microbial dihydrofolate reductase (DHFR) that is used to treat subjects with, for example, acute bacterial skin, skin structure infections (ABSSSI) and/or hospital-acquired bacterial pneumonia (HABP) and/or ventilator associated bacterial pneumonia (VABP). Iclaprim is a targeted Gram-positive broad-spectrum bactericidal antibiotic, which has a low propensity for resistance development. Iclaprim also exhibits an alternative mechanism of action against bacterial pathogens, including Gram-positive isolates of many staphylococcal, streptococcal, and enterococcal genera, as well as various Gram-positive pathogens that are resistant to antibiotic treatment; e.g., methicillin-resistant *Staphylococcus aureus* (MRSA). Iclaprim thus has the potential to be an effective drug for treating infections of bacteria that have become resistant to standard antibiotics.

Iclaprim has characteristics that, to date, have prevented it from being approved for clinical use in humans. For example, IV administration of iclaprim can potentially cause QTc prolongation in a dose-dependent manner. However, dosing of iclaprim at levels which do not produce a cardiac safety signal have not shown satisfactory clinical efficacy. In particular, Phase III clinical trials (ASSIST-1 and ASSIST-2 studies) evaluating the intravenous administration of a weight-based dose of iclaprim below that which caused QTc prolongation did not achieve satisfactory efficacy profiles, based on the non-inferiority margin of −10% as set by the Food and Drug Administration (FDA), including the failure to achieve an optimal ratio of AUC to minimum inhibitory concentration ("MIC") (AUC/MIC), time above the MIC (T>MIC) and steady-state maximal blood concentration (Cmax(ss)). See e.g., Morgan et al., Iclaprim: a novel dihydrofolate reductase inhibitor for skin and soft tissue infections, Future Microbiology, March 2009, Vol. 4, No. 2, Pages 131-144.

Accordingly, there is a need for safe and effective therapeutic methods for administration of iclaprim for treating bacterial infection.

SUMMARY

In an embodiment, the present disclosure relates to therapeutic methods comprising administering to a subject who has a bacterial infection a pharmaceutical composition comprising iclaprim, in certain embodiments the amount of iclaprim may be a fixed amount. The administration of the fixed amount can achieve a Cmax(ss). below about 800 ng/mL, a T>MIC of between about 30% to about 95% and a ratio of AUC/MIC of about 20 to about 85, and can treat the bacterial infection.

In an embodiment, the present disclosure relates to therapeutic methods comprising intravenously administering to a subject who has a bacterial infection a pharmaceutical composition comprising a fixed amount of iclaprim. The administration of the fixed amount can achieve a Cmax(ss). below about 800 ng/mL, a T>MIC of between about 30% to about 95% and a ratio of AUC/MIC of about 20 to about 85, and can treat the bacterial infection.

In other embodiments, the present disclosure provides kits comprising at least one dosage form comprising a pharmaceutical composition and therapeutic instructions for administering the at least one dosage form.

In other embodiments, the present disclosure provides dosing regimens comprising intravenously administering to a subject who has a bacterial infection a pharmaceutical composition comprising a fixed amount of iclaprim.

In other embodiments, the present disclosure provides uses of iclaprim to produce a medicament for the treatment of a bacterial infection, wherein the medicament is administered by a dosing regimen comprising administering (i.e. intravenously) to a subject who has the bacterial infection a pharmaceutical composition comprising a fixed or variable amount of iclaprim.

BRIEF DESCRIPTION OF FIGURES

FIG. 1 provides an experimental animal infection model for *S. aureus* lung infection in CF (Iclaprim vs. Vancomycin).

DETAILED DESCRIPTION

The following detailed description is exemplary and explanatory and is intended to provide further explanation of the present disclosure described herein. Other advantages, and novel features will be readily apparent to those skilled in the art from the following detailed description of the present disclosure. Texts and references mentioned herein are incorporated in their entirety, including U.S. Provisional Patent Application Ser. No. 62/331,623 filed on May 4, 2016, U.S. Provisional Patent Application Ser. No. 62/469,781 filed on Mar. 10, 2017 and U.S. patent application Ser. No. 15/586,021 filed on May 3, 2017.

Abbreviations

ABSSSI Acute bacterial skin and skin structure infections
ADME Absorption, Distribution, Metabolism, Excretion
AE Adverse Event
ALT Alanine Aminotransferase
ANOVA Analysis of Variance
AST Aspartate Aminotransferase
AUC Area under the Curve
ATCC American Type Culture Collection
b.i.d. bis in diem (twice a day)
BPS Bovine Pulmonary Surfactant
CFU Colony Forming Units
CHO Chinese Hamster Ovary
CI Confidence Interval
CL Clearance
CLSI Clinical Laboratory Standard Institute
CrCl Creatinine Clearance
Cmax Maximum Plasma Concentration
Cmax(ss) Maximum Steady-State Plasma Concentration
Cmin Minimum Plasma Concentration
Cmin(ss) Minimum Steady-State Plasma Concentration
cSSSI Complicated Skin and Skin Structure Infections
CYP Cytochrome P 450
DHFR Dihydrofolate Reductase
ED50 Effective dose in 50% of Animals
EOT End of Treatment F Female
HED Human Equivalent Dose
hERG Human Ether-à-go-go Related Gene
HPLC High Performance Liquid Chromatography
IC50 50% Inhibition Concentration
ITT Intent to treat
IV Intravenous
LD50 Lethal dose in 50% of Animals
M Male
MBC Minimum Bacterial Concentration
MCE Modified Clinically Evaluable
MIC Minimum Inhibitory Concentration
MIC50 Minimum Inhibitory Concentration for 50% of strains
MIC90 Minimum Inhibitory Concentration for 90% of strains
MITT Modified Intent-To-Treat
MRSA Methicillin-Resistant *Staphylococcus aureus*
MSSA Methicillin-Susceptible *Staphylococcus aureus*
MTD Maximum Tolerated Dose
NOAEL No Observed Adverse Effect Level
p.o. Oral (per os)
PAE Post Antibiotic Effect
PAE-SME Post-antibiotic Sub-MIC Effect
Pgp P-glycoprotein
PP Per Protocol
q12h Every 12 hours
q24h Every 24 hours
q48h Every 48 hours
QTC Corrected QT Interval
SAE Serious Adverse Event
t½ Elimination Half-life
Tmax Time to Maximum Concentration
TK Thymidine kinase
TMP Trimethoprim
TMP-SMX Trimethoprim sulfamethoxazole
ULN Upper Limit of Normal
VISA Vancomycin Intermediate *Staphylococcus aureus*
VRSA Vancomycin Resistant *Staphylococcus aureus*
Vss Volume of Distribution at Steady State The term "subject" should be construed to include subjects, for example medical or surgical subjects, such as humans and other animals suffering from bacterial infection.

Iclaprim is a diaminopyrimidine derivative that is in the same pharmacological class as trimethoprim (TMP), and which acts as a dihydrofolate reductase-inhibiting, targeted Gram antibiotic active against Gram positive organisms. The iclaprim mesylate salt has been formulated in a sterile aqueous/ethanolic vehicle as a concentrated solution for intravenous infusion after dilution for clinical testing on humans.

Iclaprim is racemic, and nomenclature for iclaprim mesylate (International Nonproprietary Name (INN)) includes IUPAC chemical name 5-[(2RS)-2-cyclopropyl-7,8-dimethoxy-2Hchromen-5-ylmethyl] pyrimidine-2,4-diamine methanesulfonate. Other names include 5-[[(2RS)-2-cyclopropyl-7,8-dimethoxy-2H-1-benzopyran-5-yl]methyl]pyrimidine-2,4-diamine methanesulfonate. The structural formula for iclaprim mesylate is:

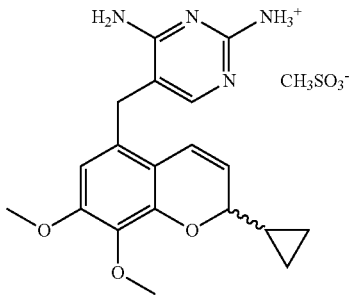

The molecular formulae for iclaprim and iclaprim mesylate are $C_{19}H_{23}N_4O_3$ (base) and $C_{20}H_{26}N_4O_6S$ (mesylate), and their relative molecular masses are 354.41 (base) or 450.52 (mesylate). General properties of iclaprim mesylate include, for example, a pH value of 4.2 for a 1% solution in water and a $pK_a$ of 7.2, a melting point range of 200-204° C., and solubility in water at 20° C. of approximately 10 mg/mL. One skilled in the art can readily obtain iclaprim or iclaprim mesylate, and synthesis of these compounds is described in U.S. Pat. No. 5,773,446, the entire disclosure of which is herein incorporated by reference.

As indicated above, pre-clinical and clinical studies indicate that iclaprim can cause QTc prolongation under certain circumstances. For example, iclaprim reversibly inhibited the hERG-mediated potassium current in transfected CHO cells, with an IC50 of 0.9 μM. In isolated rabbit Purkinje fibers, the action potential duration was increased at iclaprim concentrations above 1 μM. In contrast, the IC50 of iclaprim on the SCN5A sodium channel was found to be 95 μM and on the L-type calcium channel was found to be 46 μM, thereby suggesting that there is a selective hERG-channel inhibitory effect. Moreover, a transient QTc prolongation at Cmax was observed in human Phase I studies with iclaprim, which was pronounced at greater doses and shorter infusion times than the dose regimen foreseen for clinical use as determined by acute animal toxicity studies.

In such acute animal toxicity studies, the LD50 of IV iclaprim mesylate was determined to be >200 mg/kg in female rats and 150-200 mg/kg (HED≥20 mg/kg) in males. In the mouse, the lowest lethal IV dose was considered to be 75 mg/kg (HED 6.1 mg/kg). A repeated-dose, 4-week toxicity study was conducted in male and female rats, where single, daily IV bolus doses up to 60 mg/kg were given. In this study, histopathological changes at the injection sites were observed at dosages of 10 mg/kg/day or more, but there was no evidence of systemic toxicity. Consequently, the NOAEL was deemed to be >30 mg/kg/day (HED 3.9 mg/kg/day) of iclaprim mesylate. A 28-day toxicity study was also conducted in male and female marmosets, where iclaprim mesylate was infused intravenously over a 20-minute interval. In this study, the NOAEL was also determined to be 30 mg/kg/day (HED 3.9 mg/kg/day). In a MTD study conducted in female mini-pigs, the maximum tolerated single IV dose was determined to be 20 mg/kg (HED 14.6 mg/kg) of iclaprim mesylate.

Based on this, a single-dose ECG-study was conducted in healthy human volunteers, where 1.6 mg/kg and 3.2 mg/kg iclaprim was infused over 30 minutes. Here, iclaprim prolonged the QTc interval (QT interval corrected for heart rate) in a dose-dependent manner. Maximal increases coincided with Cmax levels and were rapidly reversible. Weight-based dosing with 1.6 mg/kg was thus assessed as acceptable for clinical purposes, whereas weight-based dosing at 3.2 mg/kg was associated with relevant QTc prolongations (>60 msec) and nonspecific T-wave alterations, and was not used for further clinical studies.

A second single-dose ECG study was conducted on healthy human volunteers using weight-based doses of 0.4 mg/kg and 0.8 mg/kg iclaprim base infused over 30 minutes and 1.6 mg/kg infused over 60 minutes. Evaluation of the QTc interval showed a reversible dose-dependent effect of iclaprim on the duration of the QTc interval at 0.8 mg/kg and 1.6 mg/kg. At both the 0.8-mg/kg and 1.6-mg/kg doses, no subject had a maximal QTc value >500 msec. When QTc was corrected according to Fridericia (QTcF), no subject exhibited any post-infusion QTcF prolongation of >60 msec from baseline. In addition, in both of the ECG studies, no gender differences concerning QTc prolongations were observed nor were any cardiovascular adverse events (AEs) reported. A transient Cmax-related mean increase in QTc corrected according to Bazett (QTcB) of approximately 10 msec was observed after infusion of 0.8 mg/kg iclaprim over 30 minutes. This transient QTc prolongation is similar to or less than QTc prolongations observed with other IV-administered antibiotics; e.g., 51 msec for erythromycin, 3 to 11 msec for clarithromycin; and 9 to 17 msec for moxifloxacin. Thus, dosing with iclaprim with 0.8 mg/kg infused over 30 minutes and 1.6 mg/kg infused over 60 minutes were assessed to be safe for clinical application. Because of concerns over partitioning of iclaprim into different tissue types and the effect this had on the pharmacokinetics of the IV administered drug, the 0.8 mg/kg iclaprim weight-based dose was chosen for further clinical studies.

For example, the PK profile of 0.8 mg/kg iclaprim administered by IV was investigated in 8 subjects with mild to moderate obesity (body mass index or "BMI" 30-40) and in 8 subjects with severe obesity (BMI >40). This study showed that AUC and Cmax increased with increasing degree of obesity. The mean Cmax was 854 ng/mL in healthy subjects, 1100 ng/mL in obese subjects (BMI ≥30 to <40) and 1328 ng/mL in severely obese subjects (BMI ≥40). Linear regression analysis indicated a strong linear relationship between AUC (and Cmax) and BMI. Thus it was clear that the body composition of the subject affected the pharmacokinetics of IV administered iclaprim, with a greater percentage of body fat causing an increase in AUC and Cmax. As higher iclaprim Cmax was associated with an increased risk of toxic effects, these results indicate that caution should be taken not to overdose a subject by administering too much iclaprim with respect to the subject's BMI. Other studies showed that moderate hepatic impairment (Child-Pugh grade B) in subjects administered IV iclaprim resulted in a 2.5 fold increase in AUC and a 1.4 fold increase in Cmax. Thus there is a risk of overdosing subjects with moderate hepatic impairment, which can be mitigated by reducing the IV iclaprim dose by about 50%.

Based on the Sponsor's analyses, one of the two Phase III clinical trials evaluating IV administration of 0.8 mg/kg iclaprim to treat subjects suffering from cSSSIs failed to show sufficient efficacy at a −10% non-inferiority margin, and the US Food and Drug Administration declined to approve this weight-based treatment for marketing. Without wishing to be bound by a particular theory, one observed disadvantage of the weight-based dosing in the previous Phase III studies is that the post-antibiotic effect achieved by the weight-based doses was not enough to sustain the T>MIC between doses. Sufficient efficacy might be achieved by increasing the amount of iclaprim administered to the subject. However, as discussed above, simply increasing the weight-based dose of iclaprim risks causing QTc prolongation.

As discussed above, iclaprim showed good anti-bacterial activity in standard rodent models of infection, and the primary PK/PD predictors for efficacy were i) the ratio of the area under the curve (AUC) to the minimum inhibitory concentration (MIC), i.e. AUC/MIC, and ii) the time above the MIC (T>MIC) expressed as a percent of the dosing interval. As discussed in more detail below, in some embodiments, the present dosing regimens produce a T>MIC of between about 30% to about 95%, for example 40% to about 70%. In some embodiments, the present dosing regimens produce further achieve a ratio of AUC/MIC of about 20 to about 85.

A thorough QTc ("TQTc") study (see Example 1 below) indicated that there was an association between the maximum QTc value and the maximum plasma iclaprim concentration (Cmax). Thus, minimization of Cmax should correspond to optimal cardiovascular safety of iclaprim. As shown in Example 1, in some embodiment of the present dosing regimens, an iclaprim steady state Cmax in a subject of about 800 ng/mL is the reference value for risk of QTc prolongation.

In an embodiment, the inventors have surprisingly discovered a therapeutic method comprising the use of iclaprim and iclaprim formulations that are effective for treating adverse pulmonary conditions, including, but not limited to lung infection and lung disease. In an embodiment, iclaprim is delivered via routes known to those skilled in the art. In an embodiment, iclaprim is delivered intravenously in a fixed dosage form. In another embodiment, iclaprim is delivered via inhalation in a fixed or variable dosage form.

In an embodiment, the inventors have surprisingly discovered a therapeutic method for treating bacterial infection using a fixed dose of iclaprim, instead of a weight-based dose. The present dosing regimen can maximize T>MIC and minimize safety risks, for example by keeping steady state Cmax below a value that is known to result in QTc prolongation, for example below 800 ng/mL. Based on data from simulations of IV iclaprim fixed-dose regimens (64 mg, 72 mg, and 80 mg) based on the post hoc estimates of iclaprim PK in 470 subjects (discussed in more detail below in the Exemplary PopPK Model section), the inventors discovered that, for example, IV administration of about an 80 mg iclaprim fixed dose as approximately a 2-hour infusion administered q12h should provide about a 28% increase in AUC/MIC and a 32% increase in the T>MIC compared to the weight-based dosing regimen used in the previous Phase III studies discussed above, while keeping the Cmax(ss) below the reference Cmax of 800 ng/mL from the TQTc study and lower than the observed mean values for Cmax at doses >0.5 mg/kg in the TQTc studies. Therefore, the regimen of a fixed dose of iclaprim, for example about 80 mg administered q12h over a 2-hour period, can maximize the antibacterial efficacy while minimizing the potential for QTc prolongation.

As stated above, the finding that the present fixed-dose IV iclaprim regimen is efficacious while minimizing QTc prolongation in a subject is surprising, since systemic exposure and maximum iclaprim plasma concentrations increase with increasing BMI. Using a fixed dose of iclaprim thus presents the risk of over-dosing in subjects with mild to moderate obesity and under-dosing in subjects with normal BMI. Those skilled in the art would therefore not be motivated to test or use a fixed dose of iclaprim to treat bacterial infections.

Certain embodiments of the present disclosure thus provide methods of intravascular, for example intravenous, administration to a subject who has a bacterial infection a pharmaceutical composition comprising a fixed amount of iclaprim. In one embodiment, the fixed amount is about 60 mg to about 85 mg, for example about 70 mg to about 80 mg. In one embodiment, the fixed amount is about 80 mg.

In one embodiment, administration of the fixed amount achieves a Cmax(ss) below about 800 ng/mL, for example about 500 ng/ml to about 700 ng/ml, and a T>MIC of between about 30% to about 95%, for example 40% to about 70%. In one embodiment, the administration of the fixed amount further achieves a ratio of AUC/MIC of about 20 to about 85, for example about 25 to 80 or about 30 to about 60.

In one embodiment, intravenous administration comprises infusing the pharmaceutical composition into the subject about 1 to about 3 times a day for one or more days. In one embodiment, intravenous administration further comprises infusing the pharmaceutical composition into the subject over a time period of about 0.75 hours to about 4 hours. For example, intravenous administration can comprise infusing the pharmaceutical composition into the subject about once a day for one or more days and over a time period of about 1 to 4 hours, twice a day for one or more days and over a time period of about 0.5 to 2 hours, or three times a day for one or more days and over a time period of about 0.75 to 3 hours. In one embodiment, intravenous administration comprises infusing the pharmaceutical composition into the subject about twice a day at substantially regular intervals (q12h) and over a time period of about 2 hours for each infusion, for one or more days.

In one embodiment, the pharmaceutical composition comprises an aqueous and/or ethanolic solution. In an embodiment, the pharmaceutical composition is reconstituted or diluted in a sterile, pharmaceutically acceptable solution prior to administration to the subject. The sterile, pharmaceutically acceptable solution can be selected, for example, from the group consisting of water, saline, lactated Ringer's solution, and Ringer's acetate solution. In one embodiment, alcohol is included for stability. When stored at 25° C., the pharmaceutical composition can be stable for a period of at least about 36 months.

In one embodiment, iclaprim is provided in a formulation as a concentrate for solution for IV use in an aqueous/ethanolic vehicle. In one embodiment, a volume of the formulated solution in ampoules (60-85 mg/5 mL) is diluted with saline to about 250-1,000 mL and infused q12h over a duration of about 120 minutes for each infusion, for one or more days.

In one embodiment, the fixed amount of iclaprim is administered according to the present methods to a subject that has moderate hepatic impairment. The fixed amount can be about half the amount administered to a subject that has substantially no hepatic impairment. The fixed amount can be about 30 mg to about 42.5 mg, for example about 35 mg to about 40 mg. The ordinarily skilled physician can readily determine whether a subject has moderate hepatic impairment using any suitable technique known in the art, for example by assessing the subject and assigning them a Child-Pugh score. A Child-Pugh score of "B" indicates moderate hepatic impairment.

In one embodiment, administration of the fixed amount of iclaprim to a subject according to the present methods treats a bacterial infection. As used herein, to treat a bacterial infection means that bactericidal or bacteriostatic activity is observed, and/or that one or more symptoms of the bacterial infection (e.g., redness, swelling, increased temperature of the infected area, presence of pus, fever, aches, chills, and the like) are reduced, ameliorated or delayed.

In one embodiment, the fixed amount of iclaprim is administered to a subject according to the present methods achieves substantially no occurrences of cardiotoxicity, for example substantially no occurrences of clinically significant QTc prolongation. This can be measured, for example, in a population of subjects to whom the fixed dose iclaprim is administered according to the present methods.

In one embodiment, kits comprising at least one dosage form comprising a pharmaceutical composition comprising iclaprim and instructions for administering the at least one dosage form as a fixed dose of iclaprim according to the present methods are provided. The pharmaceutical composition can comprise one or more iclaprim pharmaceutical compositions as described above. The instructions can comprise one or more of the methods of intravenous administration as described above.

In one embodiment, dosing regimens comprising intravenously administering to a subject who has a bacterial infection a pharmaceutical composition comprising a fixed amount of iclaprim according to the present methods are provided. The pharmaceutical composition can comprise one or more compositions as described above. The intravenous administration can comprise one or more of the methods as described above.

In one embodiment, the therapeutic methods comprise administering to a subject who has a bacterial infection, a pharmaceutical composition comprising iclaprim, wherein the bacterial infection is related to or caused by skin and skin structure and/or respiratory bacterial pathogens. In an embodiment, the bacterial infection is caused by drug-resistant bacteria including wherein such bacteria is resistant to one or more drug including methicillin, daptomycin, linezolid or vancomycin. The therapeutic methods described herein comprise the treatment of infections caused by, or related to, pathogens comprising *S. pneumoniae, H. influenzae, S. aureus, K. pneumoniae* and *M. catarrhalis*. In an embodiment, the respiratory bacterial pathogens comprise methicillin-resistant *S. aureus*. In an embodiment, the bacterial infection comprises *S. aureus* lung infections, including methicillin-resistant *S. aureus* among a susceptible populations such as a cystic fibrosis population. In an embodiment, the respiratory bacterial pathogens cause, or are related to, pneumonia, asthma, emphysema and/or other adverse pulmonary conditions.

In one embodiment, uses of a medicament for producing a medicament for treating a bacterial infection, wherein the medicament is administered by a dosing regimen are provided. The medicament can comprise one or more pharmaceutical compositions as described above. The dosing regimen can comprise one or more of the methods of intravenous administration as described above.

In therapeutic applications, compositions described herein are provided to a subject suffering from bacterial infection or at risk from a bacterial infection, in an amount sufficient to delay or treat the bacterial infection. In therapeutic applications, compositions described herein are provided to a subject suffering from a skin and skin structure infection and/or pulmonary infection or at risk of pulmonary infection, or pulmonary disease, in an amount sufficient to delay or treat the adverse condition. An amount of the present compositions comprising an active ingredient adequate to accomplish this is defined as a "therapeutically effective amount." The dosage to be used in the treatment of a specific case must be subjectively determined by, and would be apparent to, the ordinarily skilled physician or medical professional, according to the methods of the present disclosure. The variables involved for determining a therapeutically effective amount of the present compositions include the specific condition and the size, age, weight, gender, disease penetration, type of procedure, previous treatments and response pattern of the subject.

The pharmaceutical compositions can be administered by routes know to those skilled in the art including, intravascularly, for example intravenously. In one embodiment, the pharmaceutical compositions can be administered intravenously. In one embodiment, the pharmaceutical compositions can also be administered via inhalation or by oral administration. The present compositions can be provided as a unit dose, for example as an infusion, which taken together comprise a therapeutically effective amount. For example, a unit dose comprising a composition of the invention can be administered once daily or multiple times daily, for example 1, 2, 3, 4, 5 or 6 times in a 12 or 24 hour period. If multiple unit doses are administered in a given time period, they can be administered at substantially even time intervals. For example, if two unit doses are administered in a 12 hour period, they can be given to the subject approximately 6 hours apart. In one embodiment, two unit doses are administered to a subject in a 24 hour period approximately 12 hours apart. Multiple unit doses are administered in a given time period can also be administered at substantially uneven time intervals. In one embodiment, a unit dosage form comprises a composition of the invention in the form of an injectable infusion for intravenous administration.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are illustrative only, since alternative methods can be utilized to obtain similar results.

Example 1

Exemplary Population PK Model

The inventors developed an exemplary Population PK ("PopPK") model for subjects with cSSSI from the Phase III "ASSIST-1" and "ASSIST-2" combined data. The PopPK analysis of the data from the ASSIST studies demonstrated no relationship between the clearance (CL) of iclaprim and body weight, leading the inventors to consider a fixed-dose rather than a weight-based dose of iclaprim, despite the risk of inducing QTc prolongation in treatment subjects. The pharmacokinetic model, based on a population PK analysis of data collected during the Phase III ASSIST clinical trials, was used to estimate the exposure to iclaprim after various fixed dosing regimens. The projected exposure profiles were assessed for their impact on PK parameters previously demonstrated to be relevant to the known safety and efficacy profile of iclaprim. Specifically, the various fixed dose regimens were examined with respect to maximizing the critical efficacy parameters, AUC/MIC and T>MIC, while minimizing Cmax, the parameter previously shown to be most closely correlated with increases in QTc. Dose selections were made based upon comparison to the "base case" regimen used in ASSIST-1 and ASSIST-2, which was a weight-based iclaprim dose of 0.8 mg/kg administered as a 0.5 hr infusion, q12h.

An iclaprim fixed dose of 80 mg administered over 2 hours every 12 hours (q12h) for 5 to 14 days was selected as the dosing regimen to be progressed in pivotal Phase III clinical studies based upon exposure projections. However, the PopPK model showed that other fixed doses would also produce the desired efficacy while minimizing the safety profile.

The selected 80 mg fixed dose was designed to optimize the efficacy and safety profiles of iclaprim based on the following considerations:

When iclaprim was tested in standard rodent models of infection, good efficacy was observed. The primary PK/PD predictors for efficacy were determined to be i) the ratio of the area under the curve (AUC) to the minimum inhibitory concentration (MIC), i.e. AUC/MIC, and ii) the time above the MIC, i.e. T>MIC, expressed as a percent of the dosing interval. Thus, optimization of these two parameters was a goal of the model.

A thorough QTc (TQTc) study indicated that there was an association between the maximum QTc value and the maximum plasma iclaprim concentration (Cmax). Thus, minimization of Cmax would be expected to correspond to optimal cardiovascular safety of iclaprim. In the TQTc study, doses of 1 mg/kg and 2 mg/kg administered over 0.5 hours led to dose-related increases in the QTc, whereas 0.5 mg/kg administered over 0.5 hours did not. The increases in QTc for the 1 mg/kg dose were considered to be mild, with a mean (95% confidence interval) change in the placebo- and baseline-corrected QTcB of 10.3 (3.3, 17.3) msec. This dose was associated with a geometric mean (95% confidence interval) Cmax of 792 (682, 919) ng/mL. A reference Cmax of 800 ng/mL was therefore used for the evaluation of potential dosing regimens with respect to the risk of QTc prolongation.

Iclaprim was administered at a dose of 0.8 mg/kg over 0.5 hours q12h for 7 to 10 days in the ASSIST-1 and ASSIST-2 trials to 500 subjects. Iclaprim was well tolerated in both studies at this dose. Adverse events (AE) related to QTc prolongation were reported infrequently (4 cases in the iclaprim arms and 2 cases in the linezolid arms) and no cases of QTc prolongation-related cardiac effects classified as treatment related AEs were observed in these studies. Iclaprim led to a mean increase of the QTc interval by about 4 to 6 msec greater than that observed with linezolid, a drug that is considered to cause QTC prolongation.

The ASSIST-1 and ASSIST-2 studies used sparse sampling with a population PK analysis. The post-hoc estimates of the individual subject PK parameters were used to simulate the plasma iclaprim concentration-time profiles for each subject and, from those profiles, the corresponding values for Cmaxss, AUC0-24 hss, AUC/MIC, and T>MIC. In these analyses, the MIC value used was based on the MIC$_{90}$ of $S.$ $aureus$ of 120 ng/mL, identified in worldwide surveillance studies. Various fixed dose regimens were examined with respect to maximizing AUC/MIC and T>MIC while minimizing the probability of a steady-state Cmax (Cmaxss)≥800 ng/mL.

The calculated parameters for the proposed fixed doses of 64 mg, 72 mg, or 80 mg, administered over 1 or 2 hours every 12 hours are compared in Table 1 to the base case, 0.8 mg/kg administered over 0.5 hr every 12 hours (the dosing regimen used in the ASSIST studies). For the base case, the median AUC0-24 hss was 3865 hr×ng/mL, the AUC/MIC was 32 and T>MIC was 39.17% (Table 1). While the predicted median Cmaxss for the base case regimen was 702 ng/mL, less than the reference Cmax from the TQTc study of 800 ng/mL, Cmaxss exceeded 800 ng/mL between the median (702 ng/mL) and the 75th percentile (953 ng/mL) (Table 1).

Examination of fixed doses of 64 mg, 72 mg, and 80 mg using a 1 hr infusion regimen (Table 1) indicates that while there is some improvement in AUC/MIC and T>MIC compared to the base case, the median Cmaxss is lower for 64 mg/1 hr but is increased for the 72 mg/1 hr and 80 mg/1 hr regimens, suggesting a potential increased risk of QTc prolongation at the higher doses infused over 1 hr as compared to the regimen used in the ASSIST trials.

The higher Cmaxss associated with the 1 hr infusions of 72 mg or 80 mg can be mitigated by extending the administration from 1 to 2 hr while maintaining similar overall exposure. The median AUC0-24 hss for the 72 mg/2 hr and 80 mg/2 hr regimens were higher than for the base case, 4466 vs. 3875 hr×ng/mL and 4962 vs. 3875 hr×ng/mL, respectively (Table 1). These projected AUCs are somewhat higher than those achieved in Phase I clinical studies in which iclaprim was safe and well tolerated (Table 2) and represent a 1.15-fold and 1.28-fold increase over those calculated for the base case exposure from the ASSIST-1 and ASSIST-2 trials. However, these levels are significantly below the AUCs achieved at the NOAEL in the 13-week toxicology studies (26,900 hr×ng/mL (males) and 26,600 hr×ng/mL (females) in the marmoset and 7260 hr×ng/mL (males) and 20,400 hr×ng/mL (females) in the rat.

The median Cmaxss for the 72 mg/2 hr and 80 mg/2 hr regimens is projected to be 590 ng/mL and 655 ng/mL, respectively (Table 1), lower than the 702 ng/mL predicted for the base case and lower than the observed mean values for Cmax observed at doses associated with QTc prolongation in the TQTc studies (Table 2). For both regimens, the upper limit of the 95% confidence interval for Cmax for the 1 mg/kg dose in the TQTc study, 919 ng/mL was not exceeded until the 90th percentile (Table 1), suggesting a good safety margin.

As mentioned above, based on animal models of infection, the efficacy of iclaprim is a function of both AUC/MIC ratio and T>MIC. As a consequence of the higher AUC that can be achieved by giving a higher dose with a longer infusion time to reduce the Cmax, the median AUC/MIC ratio is also projected to be higher for both the 80 mg/2 hr regimen (41 hr) and the 72 mg/2 hr regimen (37 hr), improvements of 1.28- and 1.16-fold, respectively, as compared to the base case (32 hr, Table 1). Similarly, the T>MIC is also projected to be higher for both the 72 mg/2 hr and 80 mg/2 hr regimens compared to the base case, with median T>MIC of 48.33% and 51.67% of the dosing interval, respectively (Table 1), 1.23- and 1.32-fold greater than the base case value of 39.17%. For both regimens, the median Cmaxss was lower than for the base case used in the ASSIST trials, 590 ng/mL and 655 ng/mL, respectively, for 72 mg/2 hr and 80 mg/2 hr (Table 1), representing respectively 84% and 93% of the median value of 702 ng/mL for the base case, thus optimizing the margin of safety.

Thus, the data from the simulations of the fixed dose regimens based on the post-hoc estimates of iclaprim PK in 500 subjects indicate that administration of 80 mg as a 2 hr infusion should provide a 28% increase in AUC/MIC and a 32% increase in the T>MIC compared to the dosing regimen used in the previous ASSIST trials, while keeping Cmaxss below the reference Cmax of 800 ng/mL (as determined from the TQTc study) and lower than the observed mean values for Cmax at doses >0.5 mg/kg in the TQTc studies. Therefore, the regimen of 80 mg fixed dose administered over 2 hr Q12H can maximize the likelihood of antibacterial efficacy while minimizing the potential for QTc prolongation. The other fixed dose dosing regimens modelled also showed acceptable efficacy while minimizing the potential for QTc prolongation.

TABLE 1

Comparison of Exposure Metrics Among Projected Iclaprim Dosing Regimens

| Parameter | Regimen | 5th | 10th | 25th | Median | 75th | 90th | 95th |
|---|---|---|---|---|---|---|---|---|
| Cmax$_{ss}$ (ng/mL) | 0.8 mg/kg/0.5 hr | 405 | 472 | 572 | 702 | 953 | 1,327 | 1,549 |
| | 64 mg/1 hr | 383 | 431 | 508 | 647 | 854 | 1,143 | 1,276 |
| | 72 mg/1 hr | 431 | 484 | 571 | 728 | 961 | 1,286 | 1,435 |
| | 80 mg/1 hr | 479 | 538 | 635 | 809 | 1,068 | 1,429 | 1,595 |
| | 64 mg/2 hr | 310 | 346 | 411 | 524 | 679 | 862 | 979 |
| | 72 mg/2 hr | 349 | 389 | 462 | 590 | 764 | 969 | 1,102 |
| | 80 mg/2 hr | 388 | 433 | 514 | 655 | 849 | 1,077 | 1,224 |
| T > MIC(%)† | 0.8 mg/kg/0.5 hr | 20.00 | 22.50 | 27.50 | 39.17 | 55.00 | 71.67 | 87.50 |
| | 64 mg/1 hr | 23.33 | 25.83 | 31.67 | 40.83 | 57.50 | 76.25 | 89.17 |
| | 72 mg/1 hr | 25.83 | 27.50 | 34.17 | 45.00 | 61.67 | 82.50 | 96.67 |
| | 80 mg/1 hr | 27.50 | 30.00 | 36.67 | 48.33 | 65.83 | 87.50 | 99.17 |
| | 64 mg/2 hr | 25.83 | 29.17 | 35.00 | 45.00 | 60.83 | 80.00 | 93.33 |
| | 72 mg/2 hr | 29.17 | 31.67 | 38.33 | 48.33 | 65.00 | 86.67 | 99.17 |
| | 80 mg/2 hr | 30.83 | 33.33 | 40.83 | 51.67 | 70.00 | 91.67 | 99.17 |
| AUC(0-24)$_{ss}$ (hr × ng/mL) | 0.8 mg/kg/0.5 hr | 1,979 | 2,192 | 2,892 | 3,865 | 5,394 | 6,903 | 8,168 |
| | 64 mg/1 hr | 2,145 | 2,463 | 3,092 | 3,970 | 5,540 | 6,978 | 7,781 |
| | 72 mg/1 hr | 2,414 | 2,771 | 3,479 | 4,466 | 6,233 | 7,850 | 8,754 |
| | 80 mg/1 hr | 2,682 | 3,079 | 3,865 | 4,962 | 6,926 | 8,722 | 9,726 |
| | 64 mg/2 hr | 2,145 | 2,463 | 3,092 | 3,970 | 5,540 | 6,978 | 7,781 |
| | 72 mg/2 hr | 2,414 | 2,771 | 3,479 | 4,466 | 6,233 | 7,850 | 8,754 |
| | 80 mg/2 hr | 2,682 | 3,079 | 3,865 | 4,962 | 6,926 | 8,722 | 9,726 |
| AUC/MIC (hr) | 0.8 mg/kg/0.5 hr | 16 | 18 | 24 | 32 | 45 | 58 | 68 |
| | 64 mg/1 hr | 18 | 21 | 26 | 33 | 46 | 58 | 65 |
| | 72 mg/1 hr | 20 | 23 | 29 | 37 | 52 | 65 | 73 |
| | 80 mg/1 hr | 22 | 26 | 32 | 41 | 58 | 73 | 81 |

TABLE 1-continued

Comparison of Exposure Metrics Among Projected Iclaprim Dosing Regimens

| Parameter | Regimen | Percentiles | | | | | | |
|---|---|---|---|---|---|---|---|---|
| | | 5th | 10th | 25th | Median | 75th | 90th | 95th |
| | 64 mg/2 hr | 18 | 21 | 26 | 33 | 46 | 58 | 65 |
| | 72 mg/2 hr | 20 | 23 | 29 | 37 | 52 | 65 | 73 |
| | *80 mg/2 hr* | *22* | *26* | *32* | *41* | *58* | *73* | *81* |

*All regimens are in terms of the free base and are administered Q12H. The base case is in bold text and the chosen regimen is in italic text.
†Percent of the dosing interval with a concentration >MIC.

TABLE 2

Summary of Exposure to Iclaprim in Phase I Studies

| Study | Regimen | Dose*† | Cmax (ng/mL)‡ | AUC (hr × ng/mL)‡ |
|---|---|---|---|---|
| HMR 00-038 | Single Dose | 0.25 mg/kg (5 min) | 686 ± 279 (4) | 598 ± 270 (4) |
| | | 0.5 mg/kg (5 min) | 1,913 ± 1,265 (4) | 988 ± 168 (4) |
| | | 1 mg/kg (5 min) | 4,726 ± 1,816 (4) | 2,575 ± 757 (3) |
| | | 2 mg/kg (5 min) | 8,306 ± 1,918 (4) | 4,280 ± 406 (4) |
| HMR 01-014 | Multiple Dose Q12H × 9 days | 75 mg/10% PG§ (20 min) | 1,294 (7) | 1,665 (7) |
| | | 150 mg/10% PG§ (20 min) | 2,351 (4) | 3,603 (4) |
| | | 150 mg/EtOH & NS§ (20 | 1,869 (4) | 3,221 (4) |
| HMR 02-011 | Single Dose | 2 mg/kg (0.5 hr) | 2,085 ± 514 (5) | 4,043 ± 1,345 (5) |
| | | 4 mg/kg (0.5 hr) | 4,023 ± 772 (5) | 6,814 ± 2,711 (5) |
| AR-100-ECG-002 | Single Dose | 2 mg/kg (0.5 hr) | 1,484 [22.4] (23) | 4,423 [24.1] (23) |
| | | 4 mg/kg (0.5 hr) | 2,851 [19.2] (23) | 8,894 [29.0] (23) |
| AR-100-ECG-003 | Single Dose | 0.5 mg/kg (0.5 hr) | 373 [23.2] (24) | 996 [26.8] (24) |
| | | 1 mg/kg (0.5 hr) | 792 [34.7] (24) | 1,980 [32.7] (24) |
| | | 2 mg/kg (1 hr) | 1,102 [27.1] (24) | 3,808 [32.4] (24) |

*Doses are in terms of the maleate salt of which 80% is composed of the free base, i.e. 1 mg/kg of the salt = 0.8 mg/kg of the free base.
†The duration of the injection/infusion is shown in parenthesis.
‡Arithmetic mean ± standard deviation (N) except Study HMR 01-014 for which the standard deviation was not included in the report and for Studies AR-100-ECG-002 and AR-100-ECG-003 for which the geometric mean [geometric coefficient of variation] (N) is reported.
§PG = propylene glycol; EtOH = ethanol; NS = Normal Saline Methods for the Exemplary PopPK Model A two-compartment population pharmacokinetic model was fit to Day 4 data (at steady state) from ASSIST-1 AND ASSIST-2 subjects (N=500). The model assumes that age and sex affect clearance, that severity of infection affects intercompartmental clearance, that weight affects apparent central volume of distribution and that the apparent peripheral volume of distribution is not affected by any subject characteristic. Bayesian estimates of the individual pharmacokinetic parameters were derived. These individual parameter estimates were estimated as part of the original modelling process. The individual parameters used for the calculations were not the population-typical values, but were the Bayesian estimates of each subject's own pharmacokinetic parameters of Day 4, which represent steady-state conditions and which were used to generate the individual concentration-time profiles. Based on these individual values, the derived parameters $AUC0\text{-}24\ h_{ss}$, $Cmax_{ss}$, $Cmin_{ss}$, AUC/MIC, and T>MIC were calculated.

A template data set was constructed in order to perform the calculations, which had the individual pharmacokinetic parameters embedded. Concentrations were generated using a NONMEM control stream. For each dosing strategy, concentrations were generated for 0.25, 0.5, 0.75, 1, 1.25, 1.5, 2, 3, 4, 5, 6, 7, 8, 9, 10, 11, and 12 hours post-start of infusion at steady-state (using Day 4 parameters). These simulation time points were employed in all simulations below. Finally, the 5th, 10th, 25th, median, 75th, 90th, and 95th percentiles of the iclaprim concentrations at each time point were calculated and are presented here.

PK-Exposure variables for steady-state conditions were estimated using the subject's own parameters and refer to a 24-hour time period. Area under the concentration-time curve ($AUC_{0\text{-}24\ hss}$) was calculated as AUC0-24 hss=2× Dose/Clearance for q12h dosing. For calculation of the peak or maximum concentration (Cmaxss), it was assumed that this occurred at the end of the infusion (0.5, 1 or 2 hours). Minimum or trough concentration (Cminss) was calculated as the concentration for time 0 before starting an infusion. The 5th, 10th, 25th, median, 75th, 90th, and 95th percentiles of these parameters were calculated and are presented here.

The PK/PD parameters AUC/MIC and T>MIC were calculated using each subject's individual PK parameters and the $MIC_{90}$ of *Staphylococcus aureus* (120 ng/mL). The 5th, 10th, 25th, median, 75th, 90th, and 95th percentiles of these parameters were calculated and are presented here.

The second objective of this study was met by statistically comparing the mean $AUC0\text{-}24\ h_{ss}$, $Cmax_{ss}$, $Cmin_{ss}$, and T>MIC with a repeated-measures analysis of variance (ANOVA). All pharmacokinetic parameters except T>MIC were log-transformed before analysis. Since each subject's parameters were estimated for each dosage strategy, the multiple parameters produced for each subject as repeated-measures were considered. The repeated-measures ANOVA compares the different PK parameters within a subject, which is considered a more powerful test than a method that ignores the repeated-measures structure of the data. The percentage of subjects with Cmaxss values greater than 800 ng/mL was compared across dosage strategies with a repeated-measures logistic regression.

Comparison of PK and PK/PD Parameters Across Dosing Strategies

The distributions of PK and PK/PD parameters are compared descriptively in Tables 3, 5, 6, 8, 9, 11, and 13. The mean parameters were compared statistically with a repeated-measures analysis of variance (ANOVA) or a repeated-measures logistic regression, as appropriate. These comparisons are illustrated in Tables 4, 7, 10, 12 and 14. Continuous PK parameters were log-transformed before comparison.

Comparison of $AUC_{0-24ss}$ Across Dosing Strategies

The distribution of $AUC_{0-24ss}$ was the same for the same dosing strategy given IV over different time periods (i.e., comparing 64 mg given IV over 1 hour or 2 hours). The distribution of the fixed dose of 64 mg IV over 1 hour was similar to the weight-based dosing strategy. The $AUC_{0-24ss}$ distribution was smallest for the weight-based dosing strategies and largest for the fixed dose of 80 mg (Table 3). The weight-based dosage distributions were more variable than the fixed dosages. Statistically, there were no differences between the two weight-based dosing strategies; all other doses had statistically significantly larger mean AUC0-24 ss (p-value <0.0001) (see Table 4). The distributions of $AUC_{0-24ss}$/MIC for the eight dosing strategies are presented in Table 5.

Comparison of $C_{maxss}$ across Dosing Strategies

The distribution of $C_{maxss}$ was higher for dosing strategies given IV over shorter durations. The distribution of $C_{maxss}$ for the fixed dose of 64 mg IV over 1 hour was similar to the 0.8 mg/kg IV over 1 hour. The lowest $C_{maxss}$ values were observed for the 64 mg IV over 2 hours dosing; those for the 80 mg IV over 1 hour were highest (Table 6). Statistically, all dosing strategies differed from the 0.8 mg/kg IV over 0.5 hours (p-value <0.05) (see Table 7). The distributions of $Cmax_{ss}$/MIC for the eight dosing strategies are presented in Table 8. The percentages of subjects with $Cmax_{ss}$ values above 800 ng/mL are presented in Table 9. These percentages were compared statistically with a repeated-measures logistic regression; these results are presented in Table 10.

All dosing strategies except the fixed dose of 72 mg differ statistically (p-value <0.05) from the 0.8 mg/kg IV over 0.5 hours.

Comparison of $Cmin_{ss}$ across Dosing Strategies

The distribution of $Cmin_{ss}$ was the highest in the fixed 80 mg given IV over 2 hours dose and lowest for the weight-based dose 0.8 mg/kg given IV over 0.5 hours (Table 11). Statistically, all dosing strategies differed from the 0.8 mg/kg IV over 0.5 hours (p-value <0.0001) (see Table 12).

Comparison of Percentage Time Above MIC Across Dosing Strategies

The distribution of T>MIC (%) was the highest in the fixed 80 mg over 2 hours dose and lowest for the weight-based dose given IV over 0.5 hours (Table 13). Statistically, all dosing strategies differed from the 0.8 mg/kg IV over 0.5 hours (p-value <0.0001) (see Table 14).

In summary, the data from the simulations of the fixed dose regimens based on the post-hoc estimates of iclaprim PK in 470 subjects indicate that administration of 80 mg as a 2 hr infusion should provide a 28% increase in AUC/MIC and a 32% increase in the T>MIC compared to the dosing regimen used in the previous ASSIST trials, while keeping $Cmax_{ss}$ below the reference Cmax of 800 ng/mL from the TQTc study and lower than the observed mean values for Cmax at doses >0.5 mg/kg in the TQTc studies. Therefore, the regimen of 80 mg administered over 2 hr Q12H can maximize the likelihood of antibacterial efficacy while minimizing the potential for QTc prolongation. The other fixed dose dosing regimens modelled also showed acceptable efficacy while minimizing the potential for QTc prolongation.

TABLE 3

Summary of $AUC_{0-24ss}$ percentiles across dosing strategies

| | AUC 0-24 hours Percentiles | | | | | | |
|---|---|---|---|---|---|---|---|
| Dosing Strategy | 5th | 10th | 25th | Median | 75th | 90th | 95th |
| 0.8 mg/kg 0.5 h iv | 1979 | 2192 | 2892 | 3865 | 5394 | 6903 | 8168 |
| 0.8 mg/kg 1 h iv | 1979 | 2192 | 2892 | 3865 | 5394 | 6903 | 8168 |
| 64 mg 1 h iv | 2145 | 2463 | 3092 | 3970 | 5540 | 6978 | 7781 |
| 72 mg 1 h iv | 2414 | 2771 | 3479 | 4466 | 6233 | 7850 | 8754 |
| 80 mg 1 h iv | 2682 | 3079 | 3865 | 4962 | 6926 | 8722 | 9726 |
| 64 mg 2 h iv | 2145 | 2463 | 3092 | 3970 | 5540 | 6978 | 7781 |
| 72 mg 2 h iv | 2414 | 2771 | 3479 | 4466 | 6233 | 7850 | 8754 |
| *80 mg 2 h iv* | *2682* | *3079* | *3865* | *4962* | *6926* | *8722* | *9726* |

*All regimens are in terms of the free base and are administered Q12H. The base case is in bold text and the chosen regimen is in italic text.

TABLE 4

Comparison of mean steady-state $AUC_{0-24\ hours}$ across dosing strategies.
Steady-state AUC 0-24 hours

| Comparison | Ratio of means | Standard Error | t-value | p-value | 95% CI |
|---|---|---|---|---|---|
| 0.8 mg/kg/1 h v 0.8 mg/kg/0.5 h | 100% | 0.01 | 0.00 | 1.0000 | (0.99, 1.01) |
| 64 mg/1 h v 0.8 mg/kg/0.5 h | 103% | 0.01 | 5.91 | <.0001 | (1.02, 1.05) |
| 72 mg/1 h v 0.8 mg/kg/0.5 h | 116% | 0.01 | 26.33 | <.0001 | (1.15, 1.18) |
| 80 mg/1 h v 0.8 mg/kg/0.5 h | 129% | 0.01 | 44.59 | <.0001 | (1.28, 1.31) |
| 64 mg/2 h v 0.8 mg/kg/0.5 h | 103% | 0.01 | 5.91 | <.0001 | (1.02, 1.05) |
| 72 mg/2 h v 0.8 mg/kg/0.5 h | 116% | 0.01 | 26.33 | <.0001 | (1.15, 1.18) |
| *80 mg/2 h v 0.8 mg/kg/0.5 h* | *129%* | *0.01* | *44.59* | *<.0001* | *(1.28, 1.31)* |

*All regimens are in terms of the free base and are administered Q12H. The base case is in bold text and the chosen regimen is in italic text.

TABLE 5

Summary of $AUC_{0-24ss}$/MIC percentiles across dosing strategies.

| | $AUC_{0-24ss}$/MIC Percentiles | | | | | | |
|---|---|---|---|---|---|---|---|
| Dosing Strategy | $5^{th}$ | $10^{th}$ | $25^{th}$ | Median | $75^{th}$ | $90^{th}$ | $95^{th}$ |
| 0.8 mg/kg/0.5 h | 16 | 18 | 24 | 32 | 45 | 58 | 68 |
| 0.8 mg/kg/1 h | 16 | 18 | 24 | 32 | 45 | 58 | 68 |
| 64 mg/1 h | 18 | 21 | 26 | 33 | 46 | 58 | 65 |
| 72 mg/1 h | 20 | 23 | 29 | 37 | 52 | 65 | 73 |
| 80 mg/1 h | 22 | 26 | 32 | 41 | 58 | 73 | 81 |
| 64 mg/2 h | 18 | 21 | 26 | 33 | 46 | 58 | 65 |
| 72 mg/2 h | 20 | 23 | 29 | 37 | 52 | 65 | 73 |
| *80 mg/2 h* | *22* | *26* | *32* | *41* | *58* | *73* | *81* |

*All regimens are in terms of the free base and are administered Q12H. The base case is in bold text and the chosen regimen is in italic text.

TABLE 6

Summary of $C_{maxss}$ percentiles across dosing strategies

| | $C_{maxss}$ (ng/mL) Percentiles | | | | | | |
|---|---|---|---|---|---|---|---|
| Dosing Strategy | $5^{th}$ | $10^{th}$ | $25^{th}$ | Median | $75^{th}$ | $90^{th}$ | $95^{th}$ |
| 0.8 mg/kg/0.5 h | 405 | 472 | 572 | 702 | 953 | 1327 | 1549 |
| 0.8 mg/kg/1 h | 355 | 415 | 505 | 623 | 836 | 1127 | 1261 |
| 64 mg/1 h | 383 | 431 | 508 | 647 | 854 | 1143 | 1276 |
| 72 mg/1 h | 431 | 484 | 571 | 728 | 961 | 1286 | 1435 |
| 80 mg/1 h | 479 | 538 | 635 | 809 | 1068 | 1429 | 1595 |
| 64 mg/2 h | 310 | 346 | 411 | 524 | 679 | 862 | 979 |
| 72 mg/2 h | 349 | 389 | 462 | 590 | 764 | 969 | 1102 |
| *80 mg/2 h* | *388* | *433* | *514* | *655* | *849* | *1077* | *1224* |

*All regimens are in terms of the free base and are administered Q12H. The base case is in bold text and the chosen regimen is in italic text.

TABLE 7

Comparison of mean $C_{maxss}$ (ng/mL) across dosing strategies.
$C_{maxss}$ (ng/mL)

| Comparison | Ratio of means | Standard Error | t-value | p-value | 95% CI |
|---|---|---|---|---|---|
| 0.8 mg/kg/1 h v 0.8 mg/kg/0.5 h | 87% | 0.01 | −21.70 | <.0001 | (0.86, 0.88) |
| 64 mg/1 h v 0.8 mg/kg/0.5 h | 90% | 0.01 | −16.25 | <.0001 | (0.89, 0.91) |
| 72 mg/1 h v 0.8 mg/kg/0.5 h | 102% | 0.01 | 2.53 | 0.0114 | (1.00, 1.03) |
| 80 mg/1 h v 0.8 mg/kg/0.5 h | 113% | 0.01 | 19.33 | <.0001 | (1.12, 1.14) |
| 64 mg/2 h v 0.8 mg/kg/0.5 h | 72% | 0.01 | −53.01 | <.0001 | (0.71, 0.73) |
| 72 mg/2 h v 0.8 mg/kg/0.5 h | 81% | 0.01 | −34.23 | <.0001 | (0.80, 0.82) |
| *80 mg/2 h v 0.8 mg/kg/0.5 h* | *90%* | *0.01* | *−17.42* | *<.0001* | *(0.89, 0.91)* |

*All regimens are in terms of the free base and are administered Q12H. The base case is in bold text and the chosen regimen is in italic text.

TABLE 8

Summary of $C_{maxss}$/MIC percentiles across dosing strategies.

| | $C_{maxss}$/MIC (ng/mL) Percentiles | | | | | | |
|---|---|---|---|---|---|---|---|
| Dosing Strategy | $5^{th}$ | $10^{th}$ | $25^{th}$ | Median | $75^{th}$ | $90^{th}$ | $95^{th}$ |
| 0.8 mg/kg/0.5 h | 3 | 4 | 5 | 6 | 8 | 11 | 13 |
| 0.8 mg/kg/1 h | 3 | 3 | 4 | 5 | 7 | 9 | 11 |
| 64 mg/1 h | 3 | 4 | 4 | 5 | 7 | 10 | 11 |
| 72 mg/1 h | 4 | 4 | 5 | 6 | 8 | 11 | 12 |
| 80 mg/1 h | 4 | 4 | 5 | 7 | 9 | 12 | 13 |
| 64 mg/2 h | 3 | 3 | 3 | 4 | 6 | 7 | 8 |
| 72 mg/2 h | 3 | 3 | 4 | 5 | 6 | 8 | 9 |
| *80 mg/2 h* | *3* | *4* | *4* | *5* | *7* | *9* | *10* |

*All regimens are in terms of the free base and are administered Q12H. The base case is in bold text and the chosen regimen is in italic text.

TABLE 9

Percentage of $C_{maxss}$ values >800 ng/mL.

| Dose | Cmaxss >800 |
|---|---|
| 0.8 mg/kg/0.5 h | 38.51% |
| 0.8 mg/kg/1 h | 28.30% |
| 64 mg/1 h | 30.21% |
| 72 mg/1 h | 41.70% |
| 80 mg/1 h | 51.91% |
| 64 mg/2 h | 14.47% |
| 72 mg/2 h | 21.49% |
| *80 mg/2 h* | *29.36%* |

*All regimens are in terms of the free base and are administered Q12H. The base case is in bold text and the chosen regimen is in italic text.

TABLE 10

Comparison of percentage of subjects with $C_{maxss}$ >800 ng/mL across dosing strategies.
Percentage $C_{maxss}$ >800 ng/mL

| Comparison | Odds Ratio | Standard Error | $\chi^2$ value | p-value | 95% CI |
|---|---|---|---|---|---|
| 0.8 mg/kg/1 h v 0.8 mg/kg/0.5 h | 0.63 | 0.04 | 52.52 | <.0001 | (0.56, 0.71) |
| 64 mg/1 h v 0.8 mg/kg/0.5 h | 0.69 | 0.05 | 25.16 | <.0001 | (0.60, 0.80) |
| 72 mg/1 h v 0.8 mg/kg/0.5 h | 1.14 | 0.08 | 3.48 | 0.0620 | (0.99, 1.31) |
| 80 mg/1 h v 0.8 mg/kg/0.5 h | 1.72 | 0.13 | 50.58 | <.0001 | (1.48, 2.00) |
| 64 mg/2 h v 0.8 mg/kg/0.5 h | 0.27 | 0.03 | 129.23 | <.0001 | (0.22, 0.34) |
| 72 mg/2 h v 0.8 mg/kg/0.5 h | 0.44 | 0.04 | 85.91 | <.0001 | (0.37, 0.52) |
| *80 mg/2 h v 0.8 mg/kg/0.5 h* | *0.66* | *0.05* | *25.66* | *<.0001* | *(0.57, 0.78)* |

*All regimens are in terms of the free base and are administered Q12H. The base case is in bold text and the chosen regimen is in italic text.

TABLE 11

Summary of $C_{minss}$ percentiles across dosing strategies.

| Dosing Strategy | $C_{minss}$ (ng/mL) Percentiles | | | | | | |
|---|---|---|---|---|---|---|---|
| | $5^{th}$ | $10^{th}$ | $25^{th}$ | Median | $75^{th}$ | $90^{th}$ | $95^{th}$ |
| 0.8 mg/kg/0.5 h | 3 | 7 | 12 | 22 | 44 | 70 | 98 |
| 0.8 mg/kg/1 h | 3 | 7 | 13 | 24 | 46 | 73 | 102 |
| 64 mg/1 h | 4 | 8 | 14 | 25 | 45 | 77 | 104 |
| 72 mg/1 h | 4 | 9 | 16 | 28 | 50 | 87 | 117 |
| 80 mg/1 h | 5 | 10 | 18 | 31 | 56 | 97 | 130 |
| 64 mg/2 h | 5 | 9 | 16 | 27 | 49 | 84 | 110 |
| 72 mg/2 h | 5 | 10 | 18 | 31 | 55 | 95 | 124 |
| *80 mg/2 h* | *6* | *11* | *20* | *34* | *62* | *105* | *138* |

*All regimens are in terms of the free base and are administered Q12H. The base case is in bold text and the chosen regimen is in italic text.

TABLE 12

Comparison of mean $C_{minss}$ (ng/mL) across dosing strategies.
$C_{minss}$ (ng/mL)

| Comparison | Ratio of means | Standard Error | t-value | p-value | 95% CI |
|---|---|---|---|---|---|
| 0.8 mg/kg/1 h v 0.8 mg/kg/0.5 h | 106% | 0.01 | 4.20 | <.0001 | (1.03, 1.09) |
| 64 mg/1 h v 0.8 mg/kg/0.5 h | 109% | 0.01 | 6.73 | <.0001 | (1.07, 1.12) |
| 72 mg/1 h v 0.8 mg/kg/0.5 h | 123% | 0.01 | 15.50 | <.0001 | (1.20, 1.26) |
| 80 mg/1 h v 0.8 mg/kg/0.5 h | 137% | 0.01 | 23.34 | <.0001 | (1.33, 1.40) |
| 64 mg/2 h v 0.8 mg/kg/0.5 h | 123% | 0.01 | 15.47 | <.0001 | (1.20, 1.26) |
| 72 mg/2 h v 0.8 mg/kg/0.5 h | 138% | 0.01 | 24.23 | <.0001 | (1.35, 1.42) |
| *80 mg/2 h v 0.8 mg/kg/0.5 h* | *154%* | *0.01* | *32.07* | *<.0001* | *(1.50, 1.58)* |

*All regimens are in terms of the free base and are administered Q12H. The base case is in bold text and the chosen regimen is in italic text.

TABLE 13

Summary of T > MIC (%) percentiles across dosing strategies.

| Dosing Strategy | Time above MIC (%) Percentiles | | | | | | |
|---|---|---|---|---|---|---|---|
| | $5^{th}$ | $10^{th}$ | $25^{th}$ | Median | $75^{th}$ | $90^{th}$ | $95^{th}$ |
| 0.8 mg/kg/0.5 h | 20.00 | 22.50 | 27.50 | 39.17 | 55.00 | 71.67 | 87.50 |
| 0.8 mg/kg/1 h | 21.67 | 24.17 | 30.00 | 40.42 | 56.67 | 73.75 | 90.00 |
| 64 mg/1 h | 23.33 | 25.83 | 31.67 | 40.83 | 57.50 | 76.25 | 89.17 |
| 72 mg/1 h | 25.83 | 27.50 | 34.17 | 45.00 | 61.67 | 82.50 | 96.67 |
| 80 mg/1 h | 27.50 | 30.00 | 36.67 | 48.33 | 65.83 | 87.50 | 99.17 |
| 64 mg/2 h | 25.83 | 29.17 | 35.00 | 45.00 | 60.83 | 80.00 | 93.33 |
| 72 mg/2 h | 29.17 | 31.67 | 38.33 | 48.33 | 65.00 | 86.67 | 99.17 |
| *80 mg/2 h* | *30.83* | *33.33* | *40.83* | *51.67* | *70.00* | *91.67* | *99.17* |

*All regimens are in terms of the free base and are administered Q12H. The base case is in bold text and the chosen regimen is in italic text.

TABLE 14

Comparison of mean T > MIC (%) across dosing strategies.
Time above MIC (%)

| Comparison | Difference in means | Standard Error | t-value | p-value | 95% CI |
|---|---|---|---|---|---|
| 0.8 mg/kg/1 h v 0.8 mg/kg/0.5 h | 1.62 | 0.24 | 6.70 | <.0001 | (1.15, 2.10) |
| 64 mg/1 h v 0.8 mg/kg/0.5 h | 2.55 | 0.24 | 10.52 | <.0001 | (2.08, 3.03) |
| 72 mg/1 h v 0.8 mg/kg/0.5 h | 6.25 | 0.24 | 25.78 | <.0001 | (5.78, 6.73) |
| 80 mg/1 h v 0.8 mg/kg/0.5 h | 9.42 | 0.24 | 38.83 | <.0001 | (8.94, 9.89) |
| 64 mg/2 h v 0.8 mg/kg/0.5 h | 6.02 | 0.24 | 24.81 | <.0001 | (5.54, 6.49) |
| 72 mg/2 h v 0.8 mg/kg/0.5 h | 9.78 | 0.24 | 40.35 | <.0001 | (9.31, 10.26) |
| *80 mg/2 h v 0.8 mg/kg/0.5 h* | *13.03* | *0.24* | *53.75* | *<.0001* | *(12.56, 13.51)* |

*All regimens are in terms of the free base and are administered Q12H. The base case is in bold text and the chosen regimen is in italic text.

Example 2

In Vitro Activity of Iclaprim Against Methicillin-Resistant *Staphylococcus aureus* Nonsusceptible to Daptomycin, Linezolid and Vancomycin Background:

The objective of this study was to determine the activity of iclaprim, a new generation diaminopyrimidine, against methicillin-resistant *Staphylococcus aureus* (MRSA) isolates, which were also not susceptible to daptomycin, linezolid or vancomycin.

Methods:

A total of 59 non-duplicative, non-consecutive isolates of MRSA, from the USA and Europe, which were nonsusceptible to daptomycin, linezolid or vancomycin were obtained from Eurofins or from the Network on Antimicrobial Resistance to *S. aureus* (NARSA). Antibacterial susceptibility testing was conducted on a range of MRSA strains and isolates with varying susceptibilities to several recognized antistaphylococcal antibiotics. Susceptibility testing was performed by broth microdilution in accordance with the Clinical and Laboratory and Standards Institute (CLSI) guidelines. Minimum inhibitory concentrations (MICs) were based on CLSI criteria. *S. aureus* breakpoints for daptomycin, linezolid and vancomycin are ≤1, ≤4, and ≤2 µg/mL (4-8 µg/mL were classified as vancomycin intermediate *S. aureus* and ≥16 were classified as vancomycin resistant *S. aureus*), respectively.

Results:

Iclaprim exhibited potent activity against the majority of the 59 MRSA isolates that were nonsusceptible to daptomycin, linezolid or vancomycin. Iclaprim had an MIC ≤1 µg/ml to the majority of MRSA isolates that were nonsusceptible to daptomycin (5 of 7 [71.4%]), linezolid (25 of 25 [100%]), or vancomycin (18 of 27 [66.7%]). The $MIC_{50}$ value was 0.25 µg/mL. Nine (15.2%) isolates had reduced susceptibility to iclaprim with MICs >8 µg/mL. These isolates were not clustered in time of isolate collection, infection type or geographic region.

Conclusions:

Iclaprim is active against clinical MRSA isolates, including those with nonsusceptibile phenotypes to daptomycin, linezolid or vancomycin. Continued surveillance is warranted to monitor the continued potency of iclaprim against MRSA, including MRSA isolates nonsusceptible to daptomycin, linezolid and vancomycin; as well as to detect any potential emergence of resistance.

Example 3

The Effect of Pulmonary Surfactant on the In Vitro Activity of Iclaprim Against Common Respiratory Bacterial Pathogens Introduction:

An antibacterial agent considered for the treatment of pneumonia must be active in the presence of pulmonary surfactant, a major component of epithelial lining fluid. The objective of the present study was to demonstrate the effect of pulmonary surfactant, if any, on the in vitro activity of iclaprim: the effect of bovine pulmonary surfactant (BPS), a major component of epithelial lining fluid, on the antibacterial activity of iclaprim against common Gram-positive and Gram-negative respiratory bacteria in vitro was investigated. Iclaprim inhibits bacterial dihydrofolate reductase and is highly active against common respiratory pathogens (i.e., *Streptococcus pneumoniae, Staphylococcus aureus, Haemophilus influenzae*, and *Morexella catarrhalis*) including emerging drug-resistant pathogens. The minimum inhibitory concentration (MIC) for iclaprim was determined in the presence and absence of bovine pulmonary surfactant (Survanta®). The in vitro antimicrobial activity of iclaprim against common respiratory bacteria remained unchanged in the presence of pulmonary surfactant at concentrations that antagonized the antimicrobial activity of daptomycin. Both the low MICs of iclaprim for respiratory pathogens and the lack of sensitivity of the MIC to the presence of pulmonary surfactant indicate that iclaprim could be a potential treatment for pneumonia caused by susceptible and multidrug resistant bacteria.

Methods 2.1 Collection of Bacterial Isolates:

Clinical isolates were identified by the submitting laboratories and confirmed by JMI Laboratories using standard bacteriologic algorithms and methodologies, including Matrix-Assisted Laser Desorption Ionization-Time Of Flight Mass Spectrometry (MALDI-TOF MS). When necessary, MALDI-TOF MS was performed using the Bruker Daltonics MALDI Biotyper (Billerica, Mass., USA), following manufacturer's instructions. Isolates selected were bacterial species commonly associated with pneumonia. Table 15 shows the clinical isolates, which were *S. pneumoniae* (n=2), *H. influenzae* (n=1), *M. catarrhalis* (n=2), *S. aureus* (n=1), and *Klebsiella pneumoniae* (n=1). Table 1 also shows the American Type Culture Collection (ATCC) reference strains, which were *Escherichia coli* (n=1), *Enterococcus faecalis* (n=2), *K. pneumoniae* (n=1), *S. pneumoniae* (n=2), *H. influenzae* (n=1), *M. catarrhalis* (n=1), and *S. aureus* (n=1). 2.2 Susceptibility testing

TABLE 15

Demographic data for the clinical isolates used in this study

| Species | Year | Country | Infection Type | Infection Source | Age | Gender |
|---|---|---|---|---|---|---|
| Haemophilus influenzae | 2014 | USA | Community-acquired respiratory tract infection | Tracheal aspirate | <1 | M |
| Klebsiella pneumoniae | 2014 | Mexico | Pneumonia in hospitalized patients | Tracheal aspirate | 35 | M |
| Moraxella catarrhalis | 2015 | USA | Community-acquired respiratory tract infection | Sputum | 85 | F |
| Moraxella catarrhalis | 2015 | USA | Community-acquired respiratory tract infection | Sputum | 85 | F |
| Staphylococcus aureus | 2014 | Italy | Pneumonia in hospitalized patients | Tracheal aspirate | 57 | F |
| Streptococcus pneumoniae | 2014 | USA | Bloodstream infection | Blood culture | 59 | M |
| Streptococcus pneumoniae | 2014 | Italy | Pneumonia in hospitalized patients | Pleural fluid | 68 | F |

Antibacterial susceptibility testing was measured by JMI Labs (North Liberty, Iowa, USA). Table 15 shows the demographic data for the seven nonduplicative, nonconsecutive clinical isolates used in this study, as defined above. These clinical isolates were collected from US (n=4), Mexico (n=2), and Italy (n=1). Susceptibility testing was performed by broth microdilution in accordance with the Clinical and Laboratory and Standards Institute (CLSI) guidelines M07-A10 (2015) and the standard operating procedures at JMI laboratories. Minimum inhibitory concentrations (MICs) were based on CLSI criteria (2015). There are no published breakpoints for iclaprim. *E. coli, K. pneumoniae, M. catarrhalis, E. faecalis*, and *S. aureus* were tested in cation-adjusted Mueller-Hinton broth (CA-MHB). *S. pneumoniae* were tested in CA-MHB supplemented with 2.5-5% lysed horse blood, and *H. influenza* were tested in Haemophilus test medium. Quality control and interpretation of results were performed in accordance with CLSI M100-S26 (2016) methods. QC ranges for iclaprim were those approved by CLSI and published in M100-S26 (2016). Iclaprim and comparator antibiotic MIC results were within the CLSI published ranges against *E. coli* ATCC 25922, *E. faecalis* ATCC 29212, *E. faecalis* ATCC 33186, *H. influenzae* ATCC 49247, *K. pneumoniae* ATCC 700603 (ESBL phenotype), *S. aureus* ATCC 29213, and *S. pneumoniae* ATCC 49619. Isolates were tested with MIC panels (ThermoFisher Scientific, Cleveland, Ohio, USA) of comparator antibiotics (daptomycin and levofloxacin).

Because bovine pulmonary surfactant can introduce cloudiness to the MIC testing media, antimicrobial growth inhibition was also evaluated using the colorimetric metabolic indicator resazurin (Camlab Ltd., Cambridge, UK). Following visual MIC value determinations, 10 μL of a resazurin solution (6.75-7.0 mg/mL in $H_2O$) was added to the test wells in each panel, and the panels were incubated for an additional 1-3 hours at 35° C. in ambient atmosphere (Elshikh et al., 2016; Sarker et al., 2007). *S. pneumoniae* panels were omitted from resazurin analysis because the color change was obscured by the lysed horse blood present in the test medium. Growth inhibition was then evaluated as a visible color change from blue (no growth) to pink (robust growth) and recorded as a $MIC_{RZ}$ value.

2.3 Pulmonary Surfactant Interaction

The MICs of iclaprim, levofloxacin, and daptomycin were determined against Gram-positive and Gram-negative isolates. Daptomycin was included as a positive control and levofloxacin was included as a negative control because published data showed an increase in daptomycin MICs but no increase in levofloxacin MICs in the presence of pulmonary surfactant (Silverman et al, 2005).

A new vial of bovine pulmonary surfactant (BPS; Survanta®; Abbott Laboratories, Columbus, Ohio) was utilized for each independent experiment. Each vial was mixed thoroughly and a 100 μL aliquot was spread on an agar plate, which was incubated overnight to confirm sterility. BPS was added to the MIC test medium to a final concentration of 2.5% (v/v). The concentration of surfactant was expressed in terms of percent volume of Survanta® suspension, which consisted of phospholipid (25 mg/mL) and surfactant proteins (<1 mg/mL) in 0.9% sodium chloride solution (Goerke, 1998). MICs of daptomycin were determined in CAMHB with the $Ca^{2+}$ content adjusted to 50 mg/L.

Results 3.1 Pulmonary Surfactant Interaction

Table 16 shows the MICs of iclaprim, daptomycin, or levofloxacin with or without resazurin in the presence and absence of BPS. All MICs were within the ranges published by CLSI (CLSI, 2016) with the exception of iclaprim against *E. coli* ATCC 25922, where the MICs values were one two-fold dilution below the published QC range. The MIC and $MIC_{RZ}$ values for all drug/isolate combinations were approximately the same in both the absence and presence of 2.5% (v/v) BPS. The presence of BPS had minimal or no effect on the MIC and $MIC_{RZ}$ values of iclaprim for any of the tested strains or isolates. Most MICs and $MIC_{RZ}$ values were unchanged, and where shifts were observed, these were only one drug dilution. In contrast, the MIC and $MIC_{RZ}$ of daptomycin, the positive control, against the respiratory Gram-positive strains and clinical isolates increased 16 to 128-fold to >16 μg/mL in the presence of 2.5% BPS, consistent with published data (Dallow et al., 2014; Silverman et al. 2005). As expected, the presence of BPS had little or no effect on the MIC and $MIC_2$ values of levofloxacin (as a negative control) (see Table 16).

TABLE 16 a-c: In vitro activity of iclaprim of iclaprim, daptomycin and levofloxacin in the presence and absence of 2.5% bovine pulmonary surfactant

| Species | Source | Strain/Isolate | CLSI[c] | CLSI: +BPS[c] | Resazurin | Resazurin: +BPS |
|---|---|---|---|---|---|---|
| Table 16(a): ICLAPRIM | | | | | | |
| E. coli | ATCC | 25922 | 0.5 | 0.5 | 1 | 1 |
| E. faecalis | ATCC | 29212 | <=0.015 | <=0.015 | <=0.015 | <=0.015 |
| E. faecalis | ATCC | 33186 | <=0.015 | <=0.015 | 0.03 | <=0.015 |
| H. influenzae | ATCC | 49247 | 0.12 | 0.12 | 0.25 | 0.25 |
| H. influenzae | Clinical Isolate | 824704 | 0.06 | 0.06 | 0.06 | 0.06 |
| K. pneumoniae | ATCC | 700603 | 4 | 4 | 4 | 4 |
| K. pneumoniae | Clinical Isolate | 858055 | 2 | 2 | 2 | 2 |
| M. catarrhalis | Clinical Isolate | 893806 | 4 | NI[b] | 4 | 8 |
| M. catarrhalis | Clinical Isolate | 893807 | 4 | NI | 4 | 4 |
| S. aureus | ATCC | 29213 | 0.06 | 0.06 | 0.06 | 0.06 |
| S. aureus | Clinical Isolate | 825189 | 0.06 | 0.12 | 0.06 | 0.12 |
| S. pneumoniae | ATCC | 49619 | 0.06 | 0.06 | ND[a] | ND |
| S. pneumoniae | Clinical Isolate | 818757 | 0.06 | 0.06 | ND | ND |
| S. pneumoniae | Clinical Isolate | 825175 | 0.12 | 0.12 | ND | ND |
| Table 16(b): DAPTOMYCIN | | | | | | |
| E. coli | ATCC | 25922 | ND[a] | ND | ND | ND |
| E. faecalis | ATCC | 29212 | 2 | >16 | 2 | >16 |
| E. faecalis | ATCC | 33186 | 1 | >16 | 1 | >16 |
| H. influenzae | ATCC | 49247 | ND | ND | ND | ND |
| H. influenzae | Clinical Isolate | 824704 | ND | ND | ND | ND |
| K. pneumoniae | ATCC | 700603 | ND | ND | ND | ND |
| K. pneumoniae | Clinical Isolate | 858055 | ND | ND | ND | ND |
| M. catarrhalis | Clinical Isolate | 893806 | 8 | NI[b] | 8 | >16 |
| M. catarrhalis | Clinical Isolate | 893807 | 8 | NI | 8 | >16 |
| S. aureus | ATCC | 29213 | 0.5 | >16 | 0.5 | >16 |
| S. aureus | Clinical Isolate | 825189 | 0.25 | >16 | 0.25 | >16 |
| S. pneumoniae | ATCC | 49619 | 0.25 | 16 | ND | ND |
| S. pneumoniae | Clinical Isolate | 818757 | 0.25 | 16 | ND | ND |
| S. pneumoniae | Clinical Isolate | 825175 | 0.25 | 16 | ND | ND |
| E. coli | ATCC | 25922 | ND[a] | ND | ND | ND |
| E. faecalis | ATCC | 29212 | 2 | >16 | 2 | >16 |
| Table 16(c): LEVOFLOXACIN | | | | | | |
| E. coli | ATCC | 25922 | 0.015 | 0.03 | 0.015 | 0.03 |
| E. faecalis | ATCC | 29212 | 1 | 1 | 1 | 1 |
| E. faecalis | ATCC | 33186 | 4 | 1 | 4 | 2 |
| H. influenzae | ATCC | 49247 | 0.03 | 0.03 | 0.03 | 0.03 |
| H. influenzae | Clinical Isolate | 824704 | 0.015 | 0.015 | 0.015 | 0.015 |
| K. pneumoniae | ATCC | 700603 | 1 | 1 | 1 | 1 |
| K. pneumoniae | Clinical Isolate | 858055 | 0.06 | 0.12 | 0.06 | 0.06 |
| M. catarrhalis | Clinical Isolate | 893806 | 0.06 | NI[b] | 0.06 | 0.06 |
| M. catarrhalis | Clinical Isolate | 893807 | 0.06 | NI | 0.06 | 0.06 |
| S. aureus | ATCC | 29213 | 0.25 | 0.12 | 0.25 | 0.12 |
| S. aureus | Clinical Isolate | 825189 | 0.25 | 0.25 | 0.25 | 0.25 |
| S. pneumoniae | ATCC | 49619 | 1 | 1 | ND[a] | ND |
| S. pneumoniae | Clinical Isolate | 818757 | 1 | 1 | ND | ND |

TABLE 16-continued a-c: In vitro activity of iclaprim of iclaprim, daptomycin and levofloxacin in the presence and absence of 2.5% bovine pulmonary surfactant

| Species | Source | Strain/Isolate | CLSI[c] | CLSI: +BPS[c] | Resazurin | Resazurin: +BPS |
|---|---|---|---|---|---|---|
| S. pneumoniae | Clinical Isolate | 825175 | 1 | 1 | ND | ND |

[a]ND, not done (resazurin color change difficult to interpret in presence of blood)
[b]NI, not interpretable (MCAT growth difficult to interpret in the presence of BPS)
[c]CLSI, Clinical and Laboratory Standards Institute; BPS, bovine pulmonary surfactant (Survanta ®, tested at 2.5% v/v)

Discussion:

This report demonstrates that iclaprim is highly active in vitro against common respiratory bacterial pathogens (*S. pneumoniae, H. influenzae, S. aureus, K. pneumoniae* and *M. catarrhalis*) even in the presence of pulmonary surfactant. In contrast, the inhibitory effect of surfactant on antibacterial activity was observed with daptomycin in the presence of surfactant. This MIC effect of surfactant on daptomycin activity has been reported to be mediated by binding of surfactant components to specific structures present on antibiotics, such as the lipophilic side-chain of daptomycin (Silverman et al., 2005). The potency of iclaprim against common respiratory bacterial pathogens and the absence of antagonism by pulmonary surfactant of the activity in this in vitro study suggests that iclaprim should be active against pulmonary pathogens in pneumonia in vivo. In fact, a Phase 2 study comparing the clinical cure rates of two iclaprim dosages with vancomycin in the treatment of patients with nosocomial pneumonia suspected or confirmed to be caused by Gram-positive pathogens showed iclaprim and vancomycin to have comparable clinical cure rates and safety profiles. The cure rates in the intent-to-treat population were 73.9% (17 of 23), 62.5% (15 of 24), and 52.2% (12 of 23) at the post-treatment test of cure visit in the iclaprim 0.8 mg/kg intravenous (IV) q12h, iclaprim 1.6 mg/kg IV q8h, and vancomycin 1 g IV q12h group, respectively (iclaprim q12h versus vancomycin p=0.13; and iclaprim q8h versus vancomycin p=0.47). The death rates within 28 days of the start of treatment were 8.7% (2 of 23), 12.5% (3 of 24), and 21.7% (5 of 23) for the iclaprim q12h, iclaprim q8h, and vancomycin groups, respectively (no statistically significant differences). Collectively, the current in vitro study and a previous Phase 2 study support that iclaprim could be a potential treatment for pneumonia, including nosocomial pneumonia caused by susceptible and multidrug resistant Gram-positive bacteria.

Example 4

Efficacy Evaluation of Iclaprim in a Neutropenic Rat Lung Infection Model

Background:

The objective of this study was to demonstrate the effect of iclaprim in a neutropenic rat lung infection model with methicillin resistant *Staphylococcus aureus*.

Method.

*S. aureus* strain AH1252, a thymidine knockout of the MRSA wild type AW6 strain, was utilized for this study. The bacterial strain was diluted in a 2% alginate buffer, which was added dropwise in a ratio of 1:5 into 50 mM MgCl to form alginate beads. The alginate beads reduce the efficacy of bacterial clearance similar to that seen in the cystic fibrosis population. A $5.25 \times 10^4$ bacterial inoculum was administered to groups of 9 rats, intratracheally, with prepared alginate bacteria suspensions, under isoflurane anesthesia. Beginning 2 hours post infection, rats received either iclaprim or vancomycin for 3 days via subcutaneous injection every 12 hours. Twelve hours after the last treatment, rats were euthanized and lungs collected for CFU determination.

Results:

The Table 17 below shows survival, CFU/gram of lung, and change in CFUs (Standard Error of the Mean (S.E.M.) from baseline by treatment or vehicle group. FIG. 1 provides a graph showing the results for the animal infection model (iclaprim vs. vancomycin).

TABLE 17

| Group ID | Dose (mg/kg) | Total dose (mg/kg/day) | Route/regimen | Survival >60 hrs | 72 hour lungs (CFU/gram of lung) | | Change in CFUs from | |
|---|---|---|---|---|---|---|---|---|
| | | | | | $\log_{10}$CFU/Lung | S.E.M. | 2 hr. | 72 hr. |
| 2 hr inf. Controls | na | na | na | na | 3.12 | 0.53 | na | −5.56 |
| 72 hr. Inf. Controls | vehicle | na | SC/BID | 5/9 | 8.68 | 0.47 | 5.56 | na |
| Iclaprim | 80 | 160 | SC/BID | 9/9 | 3.34 | 0.46 | 0.22 | −5.34 |
| Vancomycin | 50 | 100 | SC/BID | 8/9 | 5.30 | 1.03 | 2.18 | −3.38 |

Conclusions:

In this rat lung infection model, utilizing the methicillin-resistant *S. aureus* strain AH1252, increased survival was observed in both iclaprim and vancomycin treatment groups, compared to the infection controls. Rats receiving iclaprim demonstrated a 5.34 log 10 CFU reduction from the 72 hour infection controls and only a 0.22 log 10 CFU increase from the time of treatment controls (2 hrs). Vancomycin-treated rats showed a 3.38 log 10 CFU reduction from the 72 hour infection controls and 2.18 log 10 CFU increase in CFUs from the initiation of treatment (two hours). Based on these data, therapeutic efficacy of iclaprim for subjects with *S. aureus* lung infections among the cystic fibrosis population is expected.

REFERENCES

CLSI. M07-A10. Methods for dilution antimicrobial susceptibility tests for bacteria that grow aerobically; approved standard: tenth edition. Wayne, Pa., Clinical and Laboratory Standards Institute, 2015.

Clinical and Laboratory Standards Institute. M100-S26. Performance standards for antimicrobial susceptibility testing: 26th informational supplement. Wayne, Pa.: CLSI. 2016a.

Dallow J, Otterson L G, Huband M D, Krause K M, Nichols W W. Microbiological interaction studies between ceftazidime-avibactam and pulmonary surfactant and between ceftazidime-avibactam and antibacterial agents of other classes. Int J Antimicrob Agents 2014; 44:552-6.

Elshikh M, Ahmed S, Funston S, Dunlop P, McGaw M, Marchant R, et al. Resazurin-based 96-well plate microdilution method for the determination of minimum inhibitory concentration of biosurfactants. Biotechnol Lett 2016; 38:1015-9.

EUCAST (2015). Breakpoint tables for interpretation of MICs and zone diameters. Version 5.0, January 2015.

Goerke J. Pulmonary surfactant: functions and molecular composition. Biochim Biophys Acta 1998; 1408:79-89.

Huang D, File T M Jr, Torres, A, Shorr A F, Wilcox M H, Hadvary P, et al. A Phase 2 randomized, double-blind, multicenter study to evaluate efficacy and safety of intravenous iclaprim versus vancomycin for the treatment of nosocomial pneumonia suspected or confirmed to be due to Gram-positive pathogens. Submitted.

Kompis I M, Islam K and Then R L. DNA and RNA Synthesis Antifolates Chem Rev 2005; 105:593-620.

Laue H, Valensise T, Seguin A, Lociuro S, Islam K, Hawser S. In vitro bactericidal activity of iclaprim in human plasma. Antimicrob Agents Chemother 2009; 53:4542-4.

Morrissey I, Maher K, Hawser S. Activity of iclaprim against clinical isolates of *Streptococcus pyogenes* and *Streptococcus agalactiae*. J Antimicrob Chemother. 2009; 63:413-4

Sader H S, Fritsche T R, Jones R N. Potency and bactericidal activity of iclaprim against recent clinical gram-positive isolates. Antimicrob Agents Chemother 2009; 53:2171-5.

Schneider P, Hawser S, Islam K. Iclaprim, a novel diaminopyrimidine with potent activity on trimethoprim sensitive and resistant bacteria. Bioorg Med Chem Lett 2003; 13:4217-21.

Silverman J A, Mortin L I, Vanpraagh A D, Li T, Alder J. Inhibition of daptomycin by pulmonary surfactant: in vitro modeling and clinical impact. J Infect Dis 2005; 191:2149-52.

The invention claimed is:

1. A therapeutic method consisting of:
   intravenously administering to a subject who has a bacterial infection a pharmaceutical composition consisting of a fixed amount of iclaprim,
   wherein administration of the fixed amount of iclaprim achieves a $C_{max(ss)}$ below 800 ng/mL, a T>MIC of between 30% to 95% and a ratio of AUC/MIC of 20 to 80,
   wherein the fixed amount is 80 mg,
   wherein the administration further comprises administering the pharmaceutical composition to the subject over a time period of 2 hours,
   and wherein the bacterial infection is related to respiratory bacterial pathogens.

2. The therapeutic method of claim 1, wherein the bacterial infection is caused by drug-resistant bacteria.

3. The therapeutic method of claim 2, wherein the bacteria is resistant to methicillin, daptomycin, linezolid or vancomycin.

4. The therapeutic method of claim 1, wherein the respiratory pathogens comprise *S. pneumoniae*, *H. influenzae*, *S. aureus*, *K. pneumoniae* and *M. catarrhalis*.

5. The therapeutic method of claim 4, wherein the pathogen comprises methicillin-resistant *S. aureus*.

6. The therapeutic method of claim 1, wherein the bacterial infection comprises *S. aureus* lung infections among a cystic fibrosis population.

7. The therapeutic method of claim 1, wherein the bacterial infection results in pneumonia.

8. The therapeutic method of claim 1, wherein the intravenous administration comprises infusing the pharmaceutical composition into the subject about 1 to about 3 times a day daily.

9. A dosing regimen comprising: intravenously administering to a subject who has a bacterial infection a pharmaceutical composition comprising a fixed amount of iclaprim, wherein administration of the fixed amount achieves a $C_{max(ss)}$ below 800 ng/mL, a T>MIC of between 30% to 95% and a ratio of AUC/MIC of 20 to 80,
   wherein the fixed amount is 80 mg,
   wherein the fixed amount is infused into the subject 1 to 3 times a day with each infusion taking place over a time period of 2 hours,
   and wherein the bacterial infection is related to respiratory bacterial pathogens.

10. The dosing regimen of claim 9, wherein the bacterial infection is caused by drug-resistant bacteria.

11. The dosing regimen of claim 9, wherein the bacteria is resistant to methicillin, daptomycin, linezolid or vancomycin.

12. The dosing regimen of claim 9, wherein the respiratory pathogens comprise *S. pneumoniae*, *H. influenzae*, *S. aureus*, *K. pneumoniae* and *M. catarrhalis*.

13. The dosing regimen of claim 11, wherein the pathogen comprises methicillin-resistant *S. aureus*.

14. The dosing regimen of claim 9, wherein the bacterial infection comprises *S. aureus* lung infection among a cystic fibrosis population.

15. The dosing regimen of claim 9, wherein the bacterial infection results in pneumonia.

16. The therapeutic method of claim 1, wherein the $C_{max(ss)}$ is 500 ng/ml to 700 ng/ml and the T>MIC is between 40% to 70%.

17. The therapeutic method of claim 1, wherein the administration of the fixed amount further achieves a ratio of AUC/MIC of 30 to 60.

18. The therapeutic method of claim 1, wherein the pharmaceutical composition comprises an aqueous and/or ethanolic solution.

19. The therapeutic method of claim 18, wherein the pharmaceutical composition is reconstituted or diluted in a sterile, pharmaceutically acceptable solution prior to administration to the subject.

20. The therapeutic method of claim 1, wherein the intravenous administration comprises infusing the pharmaceutical composition into the subject about 1 to about 3 times a day, for a period of 5 to 14 days.

21. The dosing regimen of claim 9, wherein the $C_{max(ss)}$ is 500 ng/ml to 700 ng/ml and the T>MIC is between 40% to 70%.

22. The dosing regimen of claim 9, wherein the administration of the fixed amount further achieves a ratio of AUC/MIC of 30 to 60.

23. The dosing regimen of claim 9, wherein the intravenous administration comprises infusing the pharmaceutical composition into the subject about 1 to about 3 times a day.

24. The dosing regimen of claim 9, wherein the pharmaceutical composition comprises an aqueous and/or ethanolic solution.

25. The dosing regimen of claim 24, wherein the pharmaceutical composition is reconstituted or diluted in a sterile, pharmaceutically acceptable solution prior to administration to the subject.

26. The dosing regimen of claim 9, wherein the intravenous administration comprises infusing the pharmaceutical composition into the subject, for a period of 5 to 14 days.

\* \* \* \* \*